United States Patent [19]
Barreto et al.

[11] Patent Number: 5,260,287
[45] Date of Patent: Nov. 9, 1993

[54] POLYPHOSPHORYLATED ORGANIC COMPOUNDS: COMPOSITIONS USEFUL IN PROTECTING BIOLOGICAL TISSUES

[75] Inventors: Jose C. Barreto, Pearland; Lenard M. Lichtenberger, Houston, both of Tex.

[73] Assignee: Board of Regents, The University of Texas System

[21] Appl. No.: 882,186

[22] Filed: May 11, 1992

[51] Int. Cl.$^5$ ............................................. A61K 31/66
[52] U.S. Cl. ...................... 514/103; 514/102; 514/108; 514/99; 514/143; 514/144; 514/925; 514/927
[58] Field of Search ............... 514/102, 103, 108, 99, 514/925, 927, 143, 144

[56] References Cited

U.S. PATENT DOCUMENTS

| | | | |
|---|---|---|---|
| 4,473,563 | 9/1984 | Nicolau et al. | 514/143 |
| 5,023,248 | 6/1991 | Siren | 514/103 |
| 5,082,833 | 1/1992 | Shamsuddin | 514/143 |

Primary Examiner—Frederick E. Waddell
Assistant Examiner—William Jarvis
Attorney, Agent, or Firm—Arnold, White & Durkee

[57] ABSTRACT

Compositions and methods for protecting the luminal lining against gastric acid challenge are disclosed. The compositions provide effective anti-ulcer preparations which include phosphorylated alcohol. Phosphorylated alcohols comprise the active anti-ulcerogenic ingredient of the described therapeutic formulations. The preparation of unique linear and cyclic polyphosphorylated alcohols and methods of using same to protect the stomach luminal lining against acid challenge are also disclosed. Inositol hexaphosphate and mannitol hexaphosphate are demonstrated to provide therapeutic value in the treatment and prevention of gastro-erosive disease precipitated by exposure of biological tissues to highly acidic substances, for example, the gastric digestive acids. While inositol hexaphosphate alone at subthreshold concentrations provides a small gastro-protective activity, a combination of inositol hexaphosphate (at subthreshold concentrations) with polyvalent cations, such as $Au^{+3}$ or $Bi^{+3}$, provides synergistic enhancement of the composition as a gastro-protective formulation.

43 Claims, 4 Drawing Sheets

FIGURE 1

POLYPHOSPHORYLATED ORGANIC COMPOUNDS: COMPOSITIONS USEFUL IN PROTECTING BIOLOGICAL TISSUES

This invention was made with government support under Grant DK33239, awarded by the National Institutes of Health. The United States government has certain rights in the invention.

BACKGROUND OF THE INVENTION

1. Field of the Invention

The present invention relates to the field of phosphorylated organic molecules, most particularly, phosphorylated alcohols. In that the compounds of the present invention may include multiple phosphate groups, the invention relates in particular to polyphosphorylated organic molecules. The present invention also relates to the field of therapeutic agents and treatment methods, as the unique anti-ulcer formulations of the present invention have been found effective in the protection of biological surfaces, particularly surfaces of the gastrointestinal tract, against acid challenge and the formation of lesions.

2. Description of the Related Art

Sufficient exposure to high concentrations of acids and other compounds, such as ethanol, is known to have a destructive effect on most tissues. However, the gastric mucosal cells of the stomach are known to secrete very high concentrations of HCL, as high as 105 mM[6]. Despite the known bio-destructive action of highly concentrated acid solutions, the cells lining the stomach are found to be protected, under healthy conditions, from the potentially destructive effects of gastric acid. Although the mechanism of this protection is not understood, the presence of a gastric mucosal barrier is frequently invoked to explain luminal acid tolerance. Supposedly, the gastric mucosal barrier functions to keep back-diffusion of acid protons into gastric tissue to a physiologically tolerable rate.

It is known that the mucosal barrier of the gastrointestinal tract provides some protection against acid challenge in an intact gastrointestinal lining. Davepport (1966) first proposed that the stomach was protected by a gastric mucosal barrier to luminal acid.[3] One proposed theory by which this bioprotective action is manifest is through the presence of the lipid bilayers, comprising the outer membrane of stomach mucosal cells, which provide a barrier to otherwise gastro-destructive substances. However, since unhealthy conditions often result in the localized loss of normal mucosal protection, researchers have sought to develop formulations and/or treatments which would artificially maintain or enhance this barrier to tissue acidification and destruction. Such a formulation would theoretically provide protection against ulceration at locations where, for whatever reason, the mucosal barrier has become compromised. Therefore, an important aspect of Applicant's invention is to provide a formulation which would provide protection to a locally compromised mucosal layer.

A variety of compositions are described as therapeutically useful in impeding gastric damage and/or protecting against ulcer formation. Particular examples of these compounds include the antacids, sucralfate-containing formulations, bismuth compounds, carbenoxolone sodium, calcium (e.g., TUMS) and sodium compounds, aluminum-containing compounds, prostaglandins (Cohen (1982)), cimetidine (i.e., Tagamet ®) and many others. However, a variety of unpleasant side affects have been associated with each of these treatments, offsetting the benefits derived from these compositions. For example, chronic administration of $H_2$ antagonists can result in an increased incidence of GI and respiratory infections. There is also concern that omeprazole and other potent $H+/K+$ ATPase inhibitors can result in premalignant gastric changes. Therefore, an important aspect of the present invention is to provide a gastro-protective formulation which minimizes and/or eliminates such side effects. Also, an object of the present invention is to provide a formulation which provides long-lasting luminal protection to the patient without other attendant unpleasant and/or detrimental side effects.

It has been reported that the protective effect provided by sulfate-containing compositions is specific for sulfate ions ($SO_4^{2-}$), and that other divalent ($HPO_4^{2-}$) and impermeant anions (gluconate-) fail to prevent acid induced decline in epithelial electrical resistance (R).[2] In these studies, the epithelial electrical resistance was correlated to the tissue-protective effect, suggesting that sulfate ion afforded protection against acid, whereas phosphate and impermanent anions did not.

New data indicates that polyphosphorylated compounds are more potent than polysulfated compounds present in sucralfates.

The general phenomenon of counter-ion diffusion has been explored in the art by Tobey et al. (1986) and Barreto et al. (1988). However, it has not heretofore been suggested that large polyphosphorylated organic compounds[11] (particularly sugars and alcohols) themselves would be effective as a gastro-protective preparation, particularly as a protective formulation for the stomach luminal lining.

Other negatively charged molecules demonstrated to have particularly low membrane permeability are the phosphorylated sugars. Phosphorylated sugars have a net negative charge. The negative charge contributed by phosphorylation prevents these phosphorylated sugars from spontaneously crossing a lipid bilayer membrane.[19] Phosphorylation of a molecule is therefore described as helping to retain the phosphorylated biomolecules themselves inside the cells (Id). However, this group of phosphorylated sugars is not described to impart any characteristic change to a membrane which would alter the membranes permeability for other molecules outside the cell. Moreover, the possible effect of a phosphorylated sugar to membrane permeability located outside a tissue or cell has similarly not been postulated.

SUMMARY OF THE INVENTION

The present invention relates to a unique compositions of matter which may also be used in therapeutic formulations. As a therapeutic formulation, the described compositions are found to have amazing bioprotective capabilities, and to be capable of providing effective protection to the gastrointestinal tract against a highly acidic gastric challenge. According to the inventors's work, the "barrier" against tissue damage from biocaustic substances may be provided through an impermeability of the lipid bilayers to counter-ion movement. The formulations and treatments of the present invention may therefore be providing the observed gastro-protective action in an animal through replacing and/or enhancing the resistance of a membrane to ion-diffusion, thereby improving the acid lesion resistant characteristics of the surface.

The therapeutic preparations of the present invention comprise compositions which include a group of phosphorylated alcohol compounds found to protect biological surfaces of the gastrointestinal tract in vivo against acid challenge, for example as against HCl challenge, and other substances, including alcohols. As these compositions have been shown to minimize gastric damage after HCl challenge in vivo, protection against gastric acid attack would similarly be provided through the administration of the described formulations to an animal.

In addition, an unexpected and surprising discovery was made with regard to bioprotective activity in mixtures of subthreshold doses of inositol hexaphosphate and polyvalent cations. Specifically, it was found that while neither polyvalent cations alone, or subthreshold concentrations of phosphorylated alcohols, such as inositol hexaphosphate alone, were able to provide any reduction in lesion formation in an animal after HCl challenge, the addition of polyvalent cations $Au^{+3}$, or $Bi^{+3}$, to subthreshold doses of inositol hexaphosphate (60 mg/kg) did provide a most unexpected and surprising bio-protective action. Thus, a mixture of polyvalent cations with subthreshold concentrations of inositol hexaphosphate provided a synergistic enhancement of bioprotective activity, most specifically to the lining of the stomach, against acid attack which was not provided with treatments of either ingredient alone.

An important object of the present invention is to provide an anti-ulcer formulation which is effective in vivo to protect against acidic luminal secretions, particularly for the treatment of persons with an already compromised luminal mucosal lining. Such a formulation comprises an ulcer protective concentration of phosphorylated organic molecules in a pharmacologically acceptable diluent. Most preferably, the phosphorylated organic molecules are polyphosphorylated. The degree of phosphorylation of the organic molecules in the preparation has been found to affect the potency of the composition as a gastro-protective treatment.

The composition is to be formulated so as to be suitable for administration to a patient either orally or parenterally. Most preferably, the composition is formulated so as to be physiologically suitable for administration as an oral treatment. Where the formulation is to be administered parenterally, the pH of the solution and other physiologically important parameters must be adjusted so as to render the treatment suitable for human administration.

The compounds of the present invention have been found to be especially efficacious in providing a bioprotective shield against highly acidic challenges to the stomach lumen in vivo. Particularly preferred embodiments of the claimed phosphorylated organic compounds comprise the polyphosphorylated alcohols.

Alcohols of any desired carbon chain length may be phosphorylated according to the present invention to provide the described formulations. These formulations may then be advantageously used for the claimed methods. In more particularly preferred embodiments of the claimed bio-protective formulations, the base alcohol molecule has a carbon backbone comprising between 3 to 10 carbons. Most preferably, the phosphorylated alcohols of the claimed composition employ alcohols having between 3- to 8- backbone carbons. The novelty of the present invention lies in part in the successful polyphosphorylation of particular long-carbon chained alcohols, and the subsequent unexpected and surprising utility these agents have for protecting the luminal lining against acid-induced stomach damage.

Most particularly preferred embodiments of the claimed phosphorylated alcohols of the present invention comprise carbon structures of an open-chain configuration. Most preferably, the claimed phosphorylated alcohols of the invention do not include metal atoms in their structure.

The most preferred embodiments of the claimed phosphorylated organic molecules comprise the polyphosphorylated alcohols, such as mannitol hexaphosphate and inositol hexaphosphate. However, any polyphosphorylated alcohol which is capable of providing luminal bio-protective activity may be employed to provide the present therapeutic methods, and are compounds considered within the scope of the present claims.

One of the most preferred phosphorylated alcohols of the present invention is the polyphosphorylated alcohol, inositol hexaphosphate. Studies in the present inventors, laboratory have demonstrated that inositol hexaphosphate possesses an unprecedented gastro-protective activity, especially when the composition is formulated to include a polyvalent cation. Particular examples of polyvalent cations include $Au^{+3}$ and $Bi^{+3}$, with $Au^{+3}$ being the most preferred.

The inventors have found that formulations which comprise inositol hexaphosphate, either alone at doses of at least 100 mg/kg, or at a lower dose of about 60 mg/kg in combination with a polyvalent cation such as $Au^{+3}$ (concentration about 0.5 mM), provide an enhancement in the bioprotective action of the formula. Specifically, mixtures of the polyphosphorylated alcohols and polyvalent cations, such as $Au^{+3}$, are demonstrated to reduce gastric lesions about 70%.

In a most particularly preferred embodiment of the claimed methods, mannitol hexaphosphate, a polyphosphorylated open carbon-chain alcohol, is to be employed as the therapeutic agent. The present invention also provides for methods of preparing the various phosphorylated alcohols. For example, a method for preparing mannitol hexaphosphate is detailed, which comprises the steps of: combining stoichiometric amounts of concentrated phosphoric acid and mannitol under reduced pressure at about 160° C. Most preferably, the phosphoric acid is used in the reaction at a concentration of 85%. Reduced pressure for the reaction procedure is most preferably provided by suction from a side arm flask, and is estimated to be approximately 50 mm Hg. The reaction mixture most preferably is heated for about 1 hour at reduced pressure, or until a brown and viscous sample forms. The brown and viscous nature of the heated sample will have the appearance of caramelized sugar.

The brown, viscous sample is then to be purified into an essentially colorless, white precipitate of mannitol hexaphosphate. Purification to form the white precipitate is most preferably accomplished through the addition of a mixture of isopropyl alcohol: ammonia: water at a 5:4:1 ratio, to the brown, viscous sample. The mixture of the sample and the alcohol: ammonia: water spontaneously causes the formation of the white precipitate.

The above protocol has generally resulted in the described precipitate with no trace of the brown color remaining. The inventors are currently developing methods whereby ammonia introduced through bubbling nitrogen through anaqueous solution of the sample may be accomplished. The polyphosphorylated forms of various other alcohols, such as glycerol, threitol, and xylitol, for example, can be synthesized in similar fashion.

Several theories are currently being investigated by the inventors to determine the mechanism by which the claimed formulations are able to provide luminal protection. While not intending to be limited to any particular theory by which the claimed invention provides the observed surprising and unexpected bioactivity, it is postulated that tissue acidification may be due to $H^+$ diffusion across a membrane bilayer, and that such ion transport may be dependent upon a counter-ion diffusion, so as to preserve net electroneutrality across the membrane.

The possibility that the polyphosphorylated compounds exert their protective effect by serving as impermeant counter-ions, thereby aiding in the inhibition of counter-ion movement, is currently being further investigated by the inventors. More specifically, the dependence of $H^+$ membrane transport upon a concurrent and opposite transport of counter-ion to the outside of the membrane is one theory proposed by the inventors as providing the mechanism by which $H^+$ diffusion, for example at the luminal membrane, may be restricted by the presence of impermeant polyphosphorylated, negatively-charged compounds.

Alternatively, while again not intending to be limited to any particular mechanism of action, the protective features of the described compositions may be attributable to the action of the large polyphosphorylated compounds at or near the surface of the gastric mucosa. Generally speaking, polyphosphorylated organic molecules (PPO's) are large impermeant anions, and are postulated by Applicants to effectively "block" the passage of other ions through the lumen membrane by providing the lumen with a protective "covering." Such large impermeant ions may not easily enter the systemic circulation. If this is in fact the case, then the compounds of the present invention would be expected to exhibit minimal side effects, since the composition would be contained locally and not be capable of entering the systemic circulation.

While again not intending to be limited to any particular theory or mechanism of action, the effectiveness of the described compositions in protecting against ulcer formation and gastric mucosal damage may be due, in whole or in part, to the ability of the composition to prevent acid-back diffusion through the stomach lining. However, it is equally as likely that the described surprisingly effective anionically-charged phosphorylated alcohols are providing a protective effect via an entirely different mechanism not described herein. The various mechanisms of action described herein are currently being examined.

Inositol hexaphosphate is one of the polyphosphorylated alcohols of the invention which may be described as "naturally occurring". However, others of the phosphorylated alcohols encompassed in the compositions of the present invention are not naturally occurring, and were synthesized as new organic molecules in the laboratory of the present inventors. Methods for preparing these synthetic phosphorylated alcohols are therefore also provided as part of the present invention. The compositions of the invention, therefore, may comprise phosphorylated alcohols which are naturally occurring molecules, synthetic molecules or a combination of both.

Prior to the present disclosure, no therapeutic uses for polyphosphorylated alcohols, particularly in the management of gastro-luminal maladies, were described or suggested in the art. It was not until the present inventors, work that the bioprotective effect of a polyphosphorylated alcohol was demonstrated.

The present invention also provides methods for the synthesis of these unique polyphosphorylated organic compounds, for example, mannitol hexaphosphate, glycerol tri-phosphate, threitol tetraphosphate, and xylitol pentaphosphate. Most specifically, the present invention provides for methods for preparing a phosphorylated alcohol having a carbon chain of 3 to 5 or 7 to 10 carbons. Therapeutic uses of these compositions in the treatment and prevention of ulcerogenic disease are also provided. In addition, the invention relates to specific methods of protecting against, as well as treating ulcer disease in an animal. This method comprises administering a therapeutically effective amount of a composition comprising an anti-ulcerogenic concentration of the described phosphorylated organic compounds in a pharmacologically acceptable diluent to an animal. The method may be used for treating and preventing this condition in several types of animals, such as the rat or the human.

In the described method, the composition would be administered following the detection of a compromised gastrointestinal condition in the patient. Most particularly, a protective effect to the luminal surface of the stomach is provided by administering the phosphorylated alcohols to a patient diagnosed to have a compromised gastrointestinal lining, for example in an animal found to have an ulcer.

For use of the present method for protecting against ulcer disease, actual peptic or mucosal destruction need not be confirmed in the animal before a treatment regimen is implemented. For such use, an animal having a condition which is characterized as "pre-ulcerogenic" may be treated with the described phosphorylated alcohol-containing compositions to prevent the formation of a full-scale ulcer.

For purposes of describing the present invention, the term "pre-ulcerogenic" condition is defined as a local defect, or excavation, of the surface of an organ or tissue located inside the body, which is produced by a sloughing of inflammatory necrotic tissue. The inflammatory necrotic tissue is caused by exposure of the surface of the internal organ or tissue to a bio-destructive material, such as an acidic or extremely basic substance. With regard in particular to the gastrointestinal tract and the stomach, the inflammatory necrotic tissue is caused, for example, by the contact of highly acidic gastric juices to surfaces of the stomach which do not have a completely intact mucosal "barrier". Such is typically the case in patients with a history of alcohol use/abuse.

It is anticipated that the present invention has one of its most therapeutic utilities in the treatment of patients who have been diagnosed as having a peptic ulcer condition.

The inventors demonstrate that pretreatment of a luminal surface with mannitol hexaphosphate (the polyphosphorylated form of mannitol) with a dose of about 100 mg/kg, will reduce lumen lesion scores in vivo up to about 50% (46.9±18%; see Table 1). Higher doses (about 250 mg/kg) of this polyphosphorylated alcohol provided complete gastro-protection against all lesionary, with a 0% lesion score being demonstrated in vivo in animals with intact luminal mucosa after acid challenge.

The inventors have discovered that phosphorylated alcohols maintain, and in some cases enhance the integrity of, the gastric mucosal barrier, thus protecting it against acidic and other biodestructive challenges. Moreover, Applicants have found that mixtures of polyphosphates with polyvalent cations, for example $Au^{3+}$ and $Bi^{3+}$, synergistically interact to provide an enhanced protective action to subthreshold concentrations of a phosphorylated compound. For example, while a subthreshold, 60 mg/kg dose, of inositol hexaphosphate (purchased from Aldrich Chem Co. (Cat #28,966-3) demonstrated a modest bioprotective action (lesion score=114±8%), the addition of $Au^{+3}$ (at 0.5 mM concentration) to the composition resulted in a significant and unexpected protective bioactivity, reducing observed lesion scores to 30% (30.9±4.3%, see Table 1).

The addition of $Bi^{+3}$ (1.0 mM) to a 60 mg/kg dose of inositol hexaphosphate resulted in a modest improvement in bioprotective activity against acid challenge, providing a reduction in lesion score from 114% to 68.0% (20%, See Table 1).

In one particularly preferred embodiment of the claimed invention, the polyphosphorylated alcohol of the formulation is inositol hexaphosphate. Most particularly, the inositol hexaphosphate is administered at a dose of about 60 mg/kg in conjunction with about 0.5 mM $Au^{+3}$.

The dose of inositol hexaphosphate found capable of providing bioprotection to the stomach lumen alone comprises a dose of between about 60 mg/kg–1000 mg/kg body weight. Most preferably, the dose of inositol hexaphosphate or mannitol hexaphosphate expected to be therapeutically effective is between 100 mg/kg to 500 mg/kg in a treatment composition which does not include a polyvalent cation. A treatment regimen of polyphosphorylated alcohol alone at a dose of at least about 250 mg/kg, without the addition of polyvalent cations, was found to be capable of providing almost complete gastro-protective action.

In still another embodiment of the claimed method for protecting an animal against ulcer disease, the phosphorylated organic compound may be selected from the group consisting of inositol hexaphosphate, glycerol triphosphate, threitol tetraphosphate, xylitol pentaphosphate, mannitol hexaphosphate, or a mixture thereof.

While not intending to be limited to any particular mode of administration, the composition may be administered parenterally or orally. Most preferably, administration of the composition is oral.

For the described methods of preventing and treating ulcerogenesis in an animal, the therapeutic formulation may comprise a mixture of the various phosphorylated alcohols in a single treatment formulation, or a formulation consisting essentially of a single phosphorylated alcohol. By way of example, the mixture of polyphosphorylated alcohols may comprise mannitol hexaphosphate and inositol hexaphosphate.

Pretreatment of an animal with the described phosphorylated alcohols, such as with inositol hexaphosphate (IHP), has been found to provide a surprisingly effective protective action to the luminal surface against acid-induces lesion formation. In fact, the herein described treatments have been found effective in protecting the luminal lining even as against the tissue destructive action of 1N concentrated hydrochloric acid.

Phosphorylation of the various alcohols to provide the phosphorylated alcohols of the invention may be accomplished using the method described by Emsley and Niazi. (*Soil Biology and Biochemistry*, 16:73–76 (1984)). A particularly preferred method for preparing the polyphosphorylated alcohols having a carbon chain of 3 to 5 or 7 to 10 carbons of the present invention comprises the steps of:

a) combining stoichiometric amounts of a phosphoric acid and an organic compound having a carbon chain of between 3 to 5 or 7 to 10 carbon atoms to from a mixture;

b) heating the mixture preferably at about 160° C. under reduced pressure an amount of time adequate for the mixture to become brown and viscous (about one hour); and c) purifying the brown and viscous mixture to form an essentially white precipitate of the polyphosphorylated compound.

This technique comprises a most preferred embodiment of the method to be used to phosphorylate alcohols such as glycerol, threitol, xylitol, and mannitol. The resulting phosphorylated alcohols most preferred according to the claimed method include glycerol triphosphate, threitol tetraphosphate and xylitol pentaphosphate. These phosphorylated alcohols are, accordingly prepared from the alcohols, glycerol, threitol or xylitol, respectively. Mannitol hexaphosphate may also be prepared according to the described method from the alcohol, mannitol.

In still another aspect of the invention, a method for preparing a therapeutic agent for the treatment of ulcer disease in an animal is provided. The method in a most preferred embodiment comprises combining a phosphorylated alcohol with a volume of distilled water sufficient to provide a therapeutically effective concentration of the phosphorylated alcohol.

Most preferably, the phosphorylated alcohol is inositol hexaphosphate, glycerol triphosphate, xylitol pentaphosphate or mannitol hexaphosphate. The therapeutically effective concentration of the phosphorylated alcohol is more specifically defined as constituting about 10 mg/ml of the phosphorylated alcohol in the diluent. The formulations may further include a therapeutically effective concentration of a polyvalent cation, such as either or both of $Au^{+3}$ or $Bi^{+3}$.

A method for preparing a therapeutic agent of the phosphorylated alcohol in a tablet form is also provided. The method, in a most preferred embodiment comprises combining the white precipitate of the phosphorylated alcohol preparation, as described herein, with a quantity of a pharmacologically acceptable tableting material sufficient to provide an about 100 mg phosphorylated alcohol tablet concentration. Tableting materials suitable for human use are described in Remingtons Pharmaceutical Sciences,[21] to which reference is specifically hereby made as being incorporated into the present Specification for details regarding standard tableting procedures well known to those of skill in the art.

The most preferred phosphorylated alcohols of the invention to be used in preparing the therapeutic agent for ulcer disease in tablet form of the present invention include inositol hexaphosphate, glycerol triphosphate, threitol tetraphosphate, xylitol pentaphosphate or mannitol hexaphosphate. The tableting ingredients may further include either or both of the polyvalent cations, $Au^{+3}$ or $Bi^{+2}$, in a therapeutically effective concentration. As will be recalled, both of these particular polyvalent cations are demonstrated to synergistically enhance the gastro-protective activity of the phosphorylated alcohols described herein, particularly in combination with inositol hexaphosphate (see Table 2).

Several abbreviations are used throughout the Application. These abbreviations include the following;

$SAL$ = saline $IHP$ = inositol hexaphosphate $INOS$ = non-phosphorylated inositol $PPO$ = phosphorylated anions $MPH$ = mannitol hexaphosphate $IHP$ = inositol hexaphosphate $Au^{+3}$ = Gold $Bi^{+3}$ = Bismuth $mg/kg$ = milligram per kilogram body weight $A$ = anion $SOS$ = sucro-octa sulfate $TMAM$ = tetramethyl ammonium

DETAILED DESCRIPTION OF THE PREFERRED EMBODIMENTS

The present invention relates to methods of protecting biological surfaces, most particularly the stomach luminal surface, against acid-induced damage. Most particularly, the present compositions and methods provide protection to the luminal lining of the stomach against strong acids, such as hydrochloric acid (1 N), and therefore are also expected to serve as an ulcer-preventive composition against acidic gastric acid challenge. Thus, the presently disclosed compositions and methods are also suitable for use in preventing ulcerogenesis.

The compositions of the present invention capable of preventing ulcer disease in an animal comprise a phosphorylated alcohol in a pharmacologically acceptable diluent. By way of example, such a diluent may comprise saline water, a Ringers solution or any pharmacologically acceptable carrier solution known to those of skill in the art. In regard to technical methods which may be used to formulate the described phosphorylated alcohols and carrier solutions for administration to an animal, details may be found regarding same in Remington's Pharmaceutical Sciences (1990)[21], which reference is specifically incorporated herein by reference for such purpose.

In particularly preferred embodiments of the invention, the phosphorylated organic compounds comprise phosphorylated and polyphosphorylated alcohols, particularly polyphosphorylated alcohols. A surprising and unexpected synergism in bioprotective activity was found to exist in mixtures of subthreshold doses of a polyphosphorylated alcohol and polyvalent cations, such as gold ($Au^+$) and bismuth ($Bi^+$). Specifically, while relatively no protection against gastric lesion in vivo was observed with low concentrations (60 mg/kg) of the polyphosphorylated alcohol (mannitol hexaphosphate) alone, and while compositions of polyvalent cations alone are insoluble and therefore unsuitable for application to an internal biological surface, compositions containing $Au^{3+}$ or $Bi^{3+}$ and the same subthreshold concentration of mannitol hexaphosphate reduced gastric lesionary some 30 to 70%.

The relatively large size of the multiply-charged anions included in the compositions of the present invention renders the claimed formulations essentially membrane impermeable. This impermeability would prevent the easy entry of the compositions into the systemic circulation, and promote their protective effects locally along the surface of the gastrointestinal tract until they are excreted. For this reason, the polyphosphate compounds disclosed herein would be expected to exhibit minimal side effects and to be relatively stable and long-acting in vivo.

By way of example, polyvalent cations found to enhance the bio-protective action of phosphorylated organic molecules include: $Au^{3+}$ and $Bi^{3+}$, and may further include $Ca^{+2}$, $Fe^{+2}$, $Fe^{+3}$, $Mg^{+2}$ and $Al^{+3}$. Specifically, the addition of $Au^{+3}$ (5mM) to an about 60 mg/kg dose of inositol hexaphosphate administered to an animal has been found by the present inventors to reduce luminal lesion score after HCl challenge from 1 14% to 30% (see Table 1) (IHS vs. IHS+$Au^{+3}$).

Generally stated, a method for preparing a phosphorylated alcohol, particularly a polyphosphorylated alcohol, comprises combining stoichiometric amounts of phosphoric acid and an alcohol having a carbon chain of between 3 to 10 carbon atoms to form a mixture, heating the mixture under reduced pressure, and purifying the mixture to form a precipitate of the phosphorylated alcohol. Most preferably, the mixture is to be heated at a temperature of about 160° C. for approximately 1 hour, which will result in the formation of a brown and viscous mixture. The precipitate formed is generally an essentially white crystalline precipitate of the phosphorylated alcohol.

The reaction pressure is most preferably to be reduced to about 50 mm Hg. In a most preferred embodiment of the method, the reaction mixture may be further purified, and any contaminating brown coloration removed, through the addition of a mixture of isopropyl alcohol:Ammonia:water in a 5:4:1 ratio to the mixture (500 mg brown mixture (in a 1 ml water)+5 ml alcohol+4 ml ammonia: 5:4:1/alcohol/ammonia/water ratio). This additional processing will render an essentially white precipitate with virtually no trace of a brown color.

Even though the present invention has been described with a certain degree of particularity, it is evident that many alternatives, modifications, and variations will be apparent to those skilled in the art in light of the following disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof unless specifically indicated to do so.

EXAMPLE 1

Synthesis of a Polyphosphorylated Organic Compound

The present example illustrates a representative procedure which could be used in the preparation of the phosphorylated organic compounds of the invention. The present example is also provided to demonstrate the method by which the polyphosphorylated alcohols employed in the present invention were prepared, and to therefore satisfy "best mode" requirements.

In a most preferred embodiment of the method, an alcohol, for example, mannitol, is converted to polyphosphorylated mannitol hexaphosphate. A preferred method for preparing this compound comprises the steps of: combining stoichiometric amounts of phosphoric acid and mannitol to form a mixture; heating the mixture to about 160° C. under reduced pressure; and purifying the mixture to form a precipitate of polyphosphorylated mannitol hexaphosphate. More specifically, the mixture was heated for a period of time sufficient to form a brown, viscous mixture. This brown mixture was then purified with a solution of isopropye alcohol:ammonia:water (ratio 5:4:1 ) until a white precipitate was recovered.

More preferably, the phosphoric acid and mannitol are mixed in a round bottom flask. Additionally, the most preferred concentration of phosphoric acid to be used in the reaction is about 85%.

The mixture most preferably is heated for about one hour at 160 degrees in order to provide the brown, viscous mixture. The reduced pressure is most preferably provided by suction from a side arm flask, and is estimated to be approximately 50 mm Hg. Skeletal representations of the structures of 3, 4, 5 and 6 carbon polyphosphorylated organic molecules, particularly, polyphosphorylated alcohols, are presented below:

(Mannitol hexaphosphate is also known as inositol hexaphosphate.)

The method outlined may be employed with any number of other alcohols, such as glycerol (a 3-carbon polyalcohol), threitol (a 4-carbon alcohol) or xylitol (a 5-carbon alcohol), wherein a stoichiometric amount of any one of these alcohols would be substituted in the above protocol for mannitol to yield the corresponding polyphosphorylated compound.

While any number of procedures may be used to prepare the phosphorylated alcohols encompassed within the scope of the present invention, a method most preferred is described in Emsley, et al., *Soil Biology and Biochemistry*, 16:73-76, which reference is specifically incorporated herein for that purpose.

Technical difficulties associated with preparing polyphosphorylated forms of inositol which the present inventors were able to overcome include the elimination of the severe foaming of the reaction mixture caused by the refluxing of condensed water dropping back into the reaction. This particular technical difficulty encountered when preparing the inositol hexaphosphate was successfully overcome by preheating the phosphoric acid under a vacuum to remove water and heating the condenser with heat tape to prevent condensation.

The resulting mixture of polyphosphorylated alcohol, for example, inositol hexaphosphate, is mot preferably purified by the addition of a mixture of isopropyl alcohol:ammonia:water solution in a 5:4:1 ratio. Purification of the brown, viscous mixture with the referenced solution yielded an essentially pure, white precipitate of the phosphorylated alcohol, mannitol hexaphosphate.

Through this procedure, mannitol in its phosphorylated form takes on a surprisingly valuable therapeutic utility, as it is demonstrated to markedly reduce gastric lesions in vivo against acid challenge and to effectively protect the gastric mucosa against acid attack in vivo.

The described product, mannitol hexaphosphate, is a member of that general class of chemical compounds known as alditols. Since alditols lack a carbonyl group, they are, of course, incapable of forming cyclic hemiacetals, and therefore exist exclusively in non-cyclic, linear forms.

Stoichiometric amounts of concentrated phosphoric acid (85%) and either glycerol (3-carbon polyalcohol), threitol (4-carbon polyalcohol), or xylitol (5-carbon polyalcohol) may be similarly processed according to the described sequence of chemical processing steps to yield their corresponding polyphosphorylated alcohol forms.

For the acid challenge studies described herein, the individual polyphosphorylated alcohols were dissolved in a pharmacologically acceptable diluent, for example, water or saline, to obtain solutions of the desired study concentrations.

EXAMPLE 2

Effects of Phosphorylation on Bioprotective Activity and Potency

The present example is provided to demonstrate the enhancement in bioactivity which occurs upon phosphorylation of an alcohol. The alcohol, inositol, will be employed as an exemplary compound to demonstrate the bioprotective action imparted to an alcohol through phosphorylation. The utility of phosphorylated alcohols as bioprotective agents is also demonstrated.

Adult male rats were pretreated with either saline, inositol (1,000 mg/kg INOS) or inositol hexaphosphate (100 mg/kg, 500 mg/kg or 100 mg/kg IHP). After 1 hour, each of the animals were intragastrically challenged with 1 ml of a 1N HCL solution. The animals were then sacrificed one hour after gastric acid challenge, and the stomach from each animal dissected out and examined. The lesion length resulting from the acid challenge was recorded for each animal in a double-blind fashion.

Figure 4:
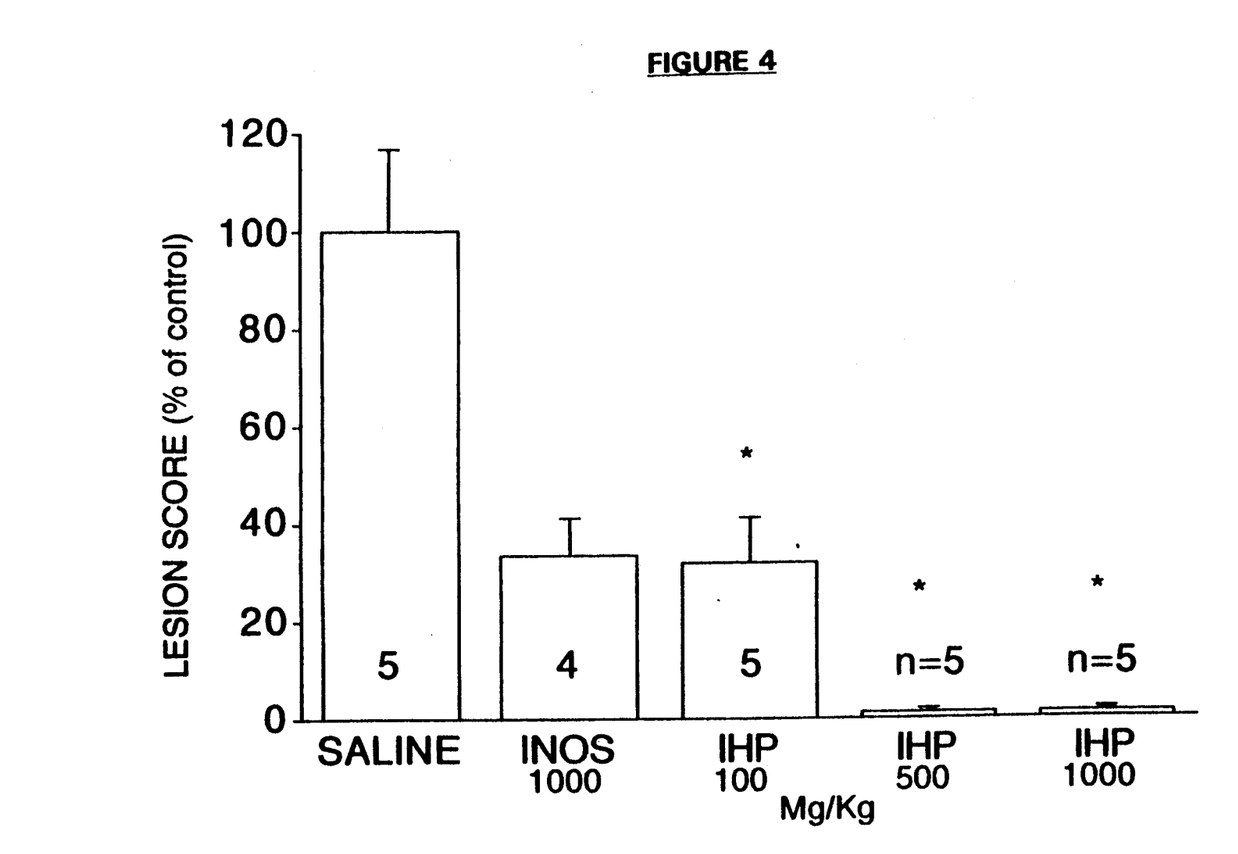
FIG. 4 In vivo protective effect of inositol and inositol hexaphosphate against HCl-induced gastric lesions in the rat. Enhancement of bioprotectivity is a function of polyphosphorylation of the alcohol.

The results from this study are presented at FIG. 4. Saline-treated animals (n=5) exhibited a lesion score of 100%. The non-phosphorylated alcohol, INOS, at a treatment dose of 1,000 mg/kg, provided some degree of gastric protection, in that a lesion score of about 35% was observed (n=4, reduction in lesion score of 65%). Animals pretreated with 1/10th the concentration of inositol hexaphosphate (IHP) (a concentration of 100 mg/ml) were found to have a lesion score equal to that of the inositol-treated group, with the lesion score being about 35% (n=5).

A dose of inositol hexaphosphate (1,000 mg/kg), equal to the high dose of inositol employed above, also provided almost complete protection against acid challenge, with a lesion score being recorded in this treatment group of only about 1% (n=5). A dose of half this concentration, 500 mg/kg inositol hexaphosphate, also provided virtually the same maximal gastroprotective effect, with lesion scores being recorded in this treatment group (n=5) of only about 1% (see FIG. 4, column 4, n=5).

The data demonstrates that phosphorylation of an alcohol results in a 30- to 40-fold enhancement in bioprotective action against acid-induced gastric lesion formation compared to the non-phosphorylated form of the alcohol at the same doses (INOS/1,000 mg/kg=35%±5% lesionary vs. IHOP/1,000 mg/kg=1%±1% lesionary). The data also demonstrates an enhancement in the potency of the alcohol as a protective agent in phosphorylated as compared to non-phosphorylated form. For example, a lesion score of 35%±5% was obtained with a pretreatment of 1,000 mg/kg INOS (inositol), the unphosphorylated form of the alcohol), while a similar reduction in lesion score was observed with only 100 mg/kg pretreatment of IHP (inositol hexaphosphate), the polyphosphorylated form of inositol.

EXAMPLE 3

In Vivo Trials with Inositol and Inositol Hexaphosphate

The present example and the examples which follow provide a model for directly comparing the activity of the various ulcer-protective compositions. These examples further provide a reasonable basis from which to determine their relative ulcer-protective efficacy and dosages in humans.

The rat model was used to evaluate the in vivo effects of a non-phosphorylated organic compound, such as inositol, and a polyphosphorylated organic compound, such as inositol hexaphosphate, and to establish the utility of employing these compounds to supply gastroprotective action in human systems.

In the present study, rats were intragastrically pretreated with 1 ml. of saline or a test solution (i.e., inositol, inositol hexaphosphate or sucrose octasulfate (sucralfate)). Gastric challenge consisted of the administration of 1 ml. of a 1.0N HCl solution or 100% ethanol 1 hour after the "pretreatment". Three different concentration doses of inositol hexaphosphate and a dodecasodium salt were used as pretreatments before gastric challenge. More particularly, inositol hexaphosphate, inositol and sucrose at 60 mg/kg, 100 mg/kg, 500 mg/kg, and 1000 mg/kg in a pharmacologically acceptable diluent (for example, saline) were tested as the pretreatment concentrations. Control animals were pretreated with saline (SAL).

The rats were sacrificed 1 hour following acid challenge (i.e, 2 hours after the pretreatment). The animals were then sacrificed and the stomachs of each of the dissectioned out. The lesion length resulting from the acid challenge was then measured and recorded for each animal stomach tissue in a double-blind fashion.

Figure 1:
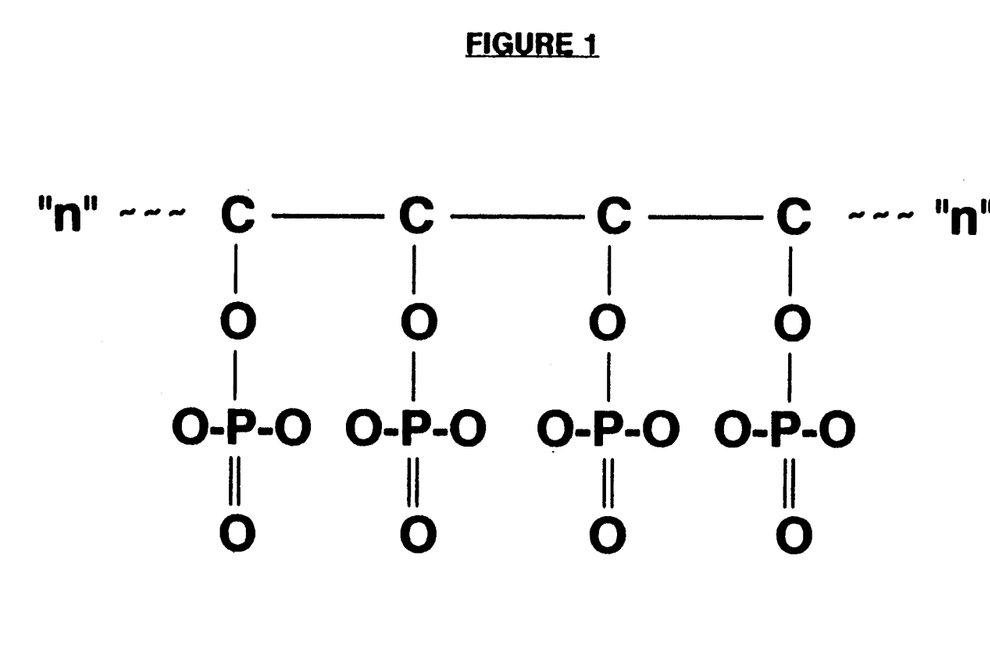
FIG. 1 General structural schematic of a phosphorylated organic compound, wherein the polyvalent anion represents—and the N represents the number of repeating units, for example, phosphorylated alcohol. Phosphorylated alcohols having either the open chain or cyclic structures of the chemical skeletal structure diagramed may be used in the bioprotective formulation of the present invention.
Figure 2:
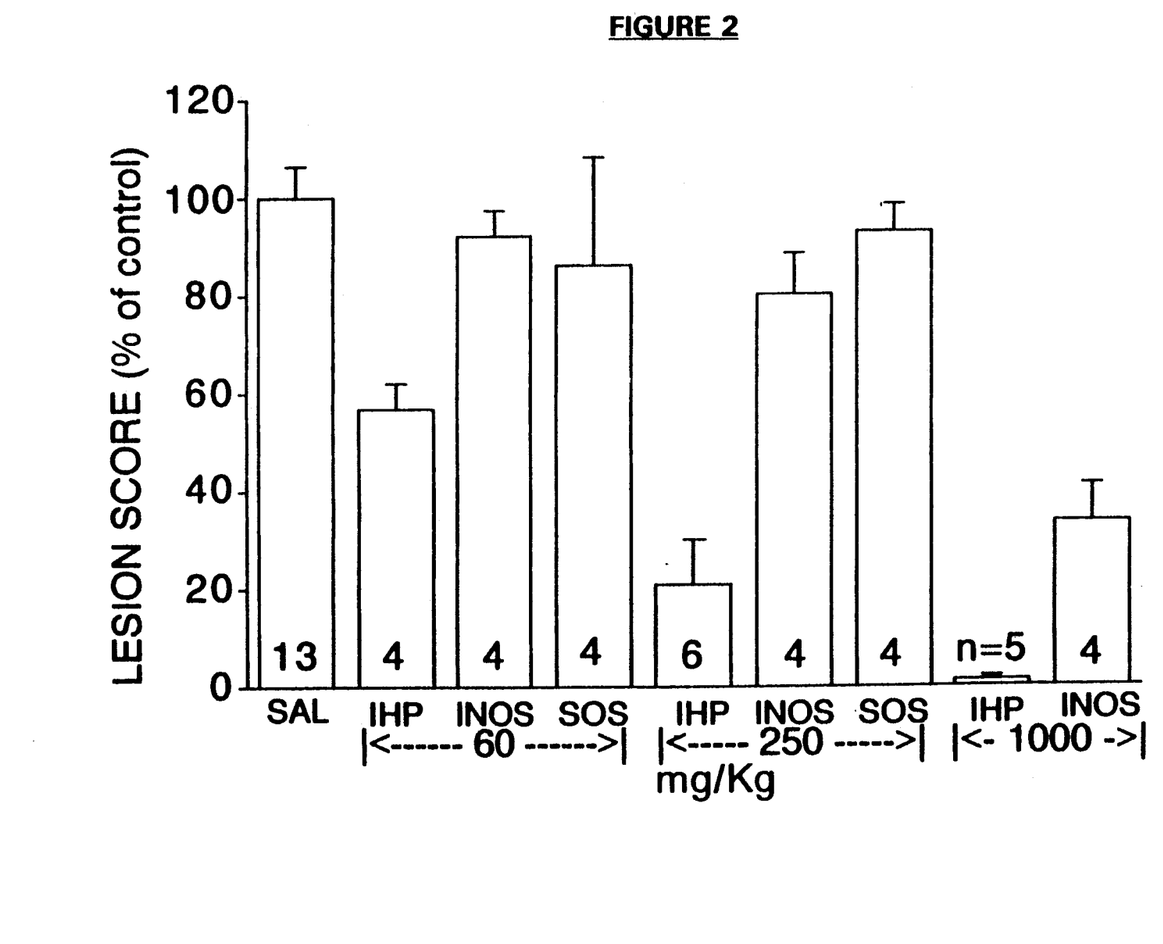
FIG. 2 Dose-dependent protective effect of inositol hexaphosphate (IHP) and myo-inositol against HCl induced gastric lesions in the rat. It should be noted that IHP is markedly more potent than other non-phosphorylated inositols (INOS), or another anionic gastroprotective compound, sucro-octa sulfate (SOS), the active ingredient in Carafate.

Results from this study are presented in FIG. 2. As demonstrated in the percent reduction in lesion score, pretreatment of animals with the tested dose of 1000 mg/ml inositol was effective in providing an about 60% reduction in lesion score (N=4), compared to non-treated saline control treated animals.

Inositol hexaphosphate at a dose of 1,000 mg/kg, was found to provide an about 90% reduction in lesion score (N=5), compared to saline treated controls. At a pretreatment dose of 250 mg/ml, a 70% reduction is lesion score (N=6), compared to saline treated controls was observed (see FIG. 2). The inositol pretreated animals demonstrated an 80% lesion score (20% reduction)

relative to control (100% lesion). Sucrose-octasulfate at 250 mg/kg provided a modest decrease in lesion length of 10%, with an about 90% lesion score relative to control (100%). The 50 mg/kg inositol hexaphosphate pretreatment elicited a 55% reduction in lesion score (N=4) compared to saline-treated controls, with inositol and sucrose-octasulfate providing less than a 10% reduction in lesion score (90% lesion and 85% lesion, respectively), relative to controls.

This example demonstrates that the polyphosphorylated form of inositol hexaphosphate was much more effective at providing gastric protection against acid challenge compared to its nonphosphorylated form, of inositol.

EXAMPLE 4

Effect of pH on In Vivo Protection of Inositol Haxaphosphate Against HCl Challenge The present example demonstrates the utility of the described polyphosphorylated alcohols in preventing and/or reducing gastric lesionary in vivo, and its therapeutic effectiveness independent of the particular pH of the solution of polyphosphorylated compounds administered to the animal.

The gastroprotective activity of the phosphorylated alcohol formulation was found to be the same with polyphosphorylated alcohol pretreatment administered at a pH of 2, 3.5, 5 and 7.

The concentration of inositol hexaphosphate used was 250 mg/kg dissolved in the pharmacologically acceptable diluent, saline, and adjusted to a pH of 2, 3.5, 5 and 7. Animals pretreated with saline at a pH of 2 (n=3) and 7 (n=5) were run concurrently as controls. Animals were treated with the individual pH-adjusted solutions of inositol hexaphosphate substantially as described in Example 2.

Figure 3:
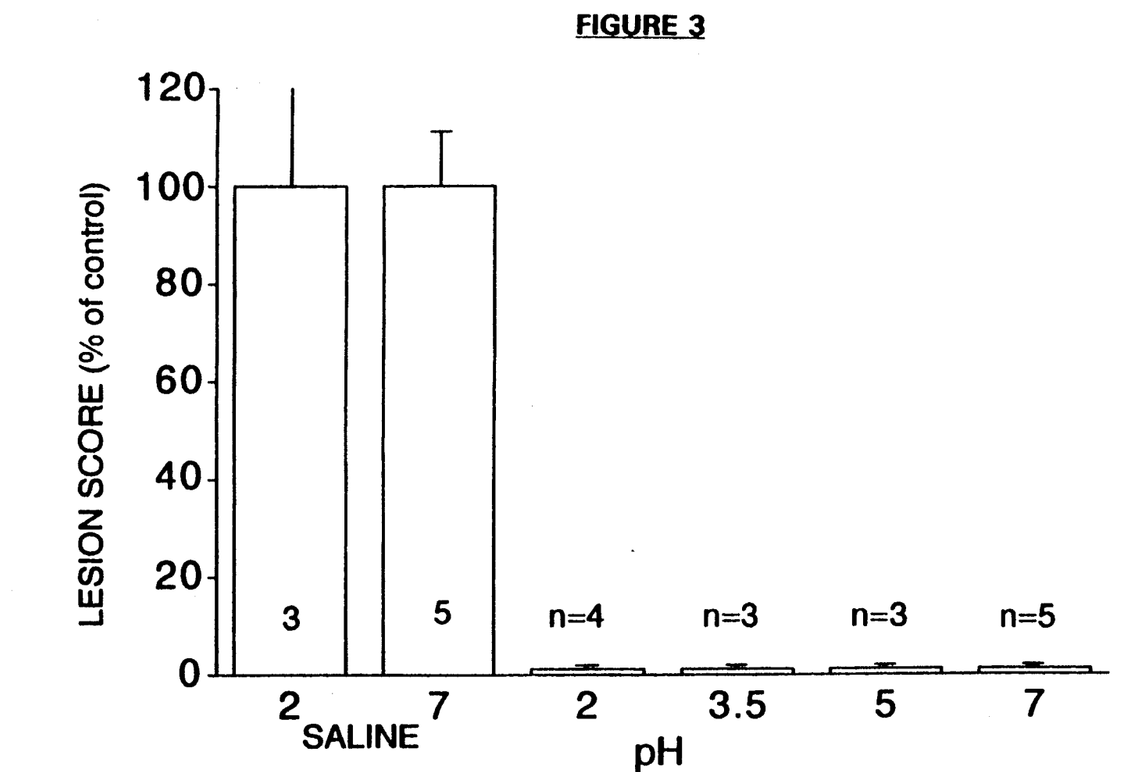
FIG. 3 In vivo protective effect of inositol hexaphosphate against HCl induced gastric lesions in the rat, is independent of the pH of the suspending solution.

As demonstrated in the data presented at FIG. 3, the protective effect of the inositol hexaphosphate was not dependent on the pH of the pretreatment solution. Lesion scores of almost 0% (i.e., 1%) were observed with all of the pH polyphosphorylated inositol pretreatments examined. As expected, saline pretreatment at both pH 2 and pH 7 experimental conditions resulted in no gastric protection, with a resulting lesion score of 100% (see FIG. 3).

These data demonstrate that the anti-lesionary protective action of inositol hexaphosphate is independent of the particular pH of the polyphosphorylated alcohol used. Also, a dose of 250 mg/kg inositol hexaphosphate was established to provide essentially complete protection against the formation of gastric lesion in response to in vivo acid challenge.

EXAMPLE 5

Phosphorylated Organic Compounds and Polyvalent Cations

The present example demonstrates the synergistic bioprotective activity which occurs in mixtures of phosphorylated alcohols and polyvalent cations. The present example also demonstrates the bioprotective action of these compositions as gastro-protective agents at relatively low doses.

In the studies previously described herein, the inventors observed that pretreatment with low doses (about 100 mg/kg) of inositol hexaphosphate (IHP) provided significant bioprotective action against lesionary. However, as demonstrated in Table 2, bioprotective action against gastric lesionary was observed with pretreatments of even lower doses (60 mg/kg) of the phosphorylated alcohols when used in conjunction with a polyvalent cation, such as $Au^{+3}$ or $Bi^{+3}$.

TABLE 2

Protective Effect of Phosphorylated Organic Compounds Against Acid-Induced Gastric Lesions

| Pretreatment | mg/kg | pH | Lesion score (% of saline control) Mean ± S.E. | (n) |
|---|---|---|---|---|
| Inositol hexaphosphate | 60 | 7 | 114 ± 8 | 5 |
| +$Au^{+3}$ (0.5 mM) | | | 30.9 ± 4.3 | 5 |
| +$Bi^{+3}$ (1.0 mM) | | | 68.0 ± 20 | 5 |
| Inositol hexaphosphate | 100 | 7 | 32.0 ± 9.6 | 5 |
| Inositol hexaphosphate | 250 | | 0 | 18 |
| Inositol hexaphosphate | 500 | | 0 | 5 |
| Mannitol hexaphosphate | 100 | 7 | 46.9 ± 18 | 5 |
| Mannitol hexaphosphate | 250 | 7 | 0 | 5 |
| Inositol | 1000 | 7 | 33.4 ± 7.8 | 5 |
| Inositol hexaphosphate | 250 | 2 | 0 | 3 |
| Inositol hexaphosphate | 250 | 3.5 | 0 | 3 |
| Inositol hexaphosphate | 250 | 5 | 0 | 3 |
| Phosphoric | (0.8 M) | 7 | 60.1 ± 16.6 | 5 |

Note: A lesion score of zero indicates that there were no observable lesions. The data are expressed as % of a control group of rats that were pretreated with saline, the lesions observed in the control group were set at 100%. A control group was run for each separate experiment.

As demonstrated in Table 2, while pretreatment of an animal with 60 mg/kg of inositol hexaphosphate alone did not provide any protection against lesion formation with acid challenge (114 of±8% (n=5) of saline control lesion score), the addition of $Au^{+3}$ (0.5 mm) to the formulation resulted in an about 70% decrease in lesion score (lesion score=30.9±4.3% (n=5) of saline control lesion score). A similar, yet less striking, reduction in bioprotective action was observed upon the addition of the polyvalent cation, $Bi^{+3}$ (1.0 mm) to the formulation, resulting in an about 30% decrease in lesion score (lesion score=68.0±20% (n=5) of saline control lesion score).

Table 2 also demonstrates potent bioprotective activity with concentrations of inositol hexaphosphate of 100 mg/kg (32.0± 9.6% lesionary), 250 mg/kg (0% lesionary) and 500 mg/kg inositol hexaphosphate treatment (0% lesionary).

The results in Table 2 also provide several other examples of phosphorylated alcohols which provide gastro-protective action to acid challenge. For example, mannitol hexaphosphate at a pretreatment concentration of 100 mg/kg resulted in an about 55% reduction in lesion score (46.9±18% (n=5) of saline control lesion score), while a 250 mg/kg pretreatment resulted in an about 100% reduction in lesion score (0% lesionary). Inositol hexaphosphate also provided nearly complete gastro-protective action, with lesion scores of 0% being observed with a 250 mg/kg pretreatment dose.

A phosphoric solution (phosphoric acid, $H_3PO_4$) at a dose of 0.8M resulted in a reduction in lesion score of about 40% (60.1±16.6% of saline control lesionary (n=5). The results demonstrate the superior bioprotective action of phosphorylated forms of alcohols, such as inositol hexaphosphate and polyphosphorylated polyalcohol, compared to the parent alcohol, such as inositol and phosphoric acid.

EXAMPLE 6

Polyphosphorylated Organic Compounds and Polyvalent Cations

The present example demonstrates the most preferred method for formulating the phosphorylated and polyphosphorylated alcohol and polyvalent cation containing preparations of the present invention. In this example, the alcohol of choice was inositol, which was polyphosphorylated to form inositol hexaphosphate. The solution of inositol hexaphosphate in a pharmacologically acceptable diluent, i.e. water, was prepared. Inositol hexaphosphate solutions were then combined with either $Au^{+3}$ (at a 0.5 mM concentration) or $Bi^{+3}$ (at a 1.0 mM concentration) polyvalent cation, in a solution where pH was adjusted to assure optimal solubility of $Au^{+3}$ or $Bi^{+3}$ (pH<3.0). The pH of the formula was then returned to neutrality before animal dosing.

One group of rats (N=5) were pretreated with inositol hexaphosphate alone at a dose of 60 mg/kg. A second group of rats (N=5) were pretreated with inositol hexaphosphate at a dose of 60 mg/kg plus $Au^{+3}$ (0.5 mM). A third group of rats (N=5) were pretreated with inositol hexaphosphate at a dose of 60 mg/kg plus $Bi^{+3}$ (1.0 mM). One hour after pretreatment, all rats were challenged with a 1N solution of HCl. One hour after HCl challenge, the animals were sacrificed. The stomachs of the animals were then dissectioned out and examined as described previously in Example 2. Lesion scores were assigned as previously described.

The results presented in Table 2, demonstrate that a 60 mg/kg dose of inositol hexaphosphate was ineffective at providing luminal protection against HCl acid challenge (114±8% lesion score). However, a mixture of 60 mg/kg inositol hexaphosphate and $Au^{+3}$ (0.5 mm) resulted in a lesion score of 30.9±4.3% (See Table 2), while a combination of inositol hexaphosphate (60 mg/kg dose) with $B:^{+3}$ (1.0 mm) provided a modest enhancement of bioprotective action compared to the low dose of inositol hexaphosphate alone, resulting in a lesion score of 68.0±20% (N=5, See Table 2).

Higher doses of inositol hexaphosphate alone at 250 mg/kg did provide complete gastric protection against acid challenge. These in vitro trials demonstrate that a synergistic enhancement of bio-protective action is imparted to subthreshold concentrations of inositol hexaphosphate (60 mg/kg) by the addition of a polyvalent cation, particularly by the addition of the polyvalent cation $Au^{+3}$ or $Bi^{+3}$ to the mixture. Because preparations of polyvalent cations alone ($Au^{+3}$ or $B^{+3}$) are insoluble at a neutral pH and form insoluble hydroxides at neutral pH (E. Brady and G. Humiston, General Chemistry, John Wiley and Sons, N.Y. p. 179, (1982[1])), such preparations would be unsuitable for application to a biological surface such as the stomach surface in vivo. Therefore, these preparations alone would be impractical and would provide no bioprotective action against stomach acid challenge in vivo.

PROPHETIC EXAMPLE 7

Proposed In Vivo Use in Humans to Prevent and Treat Ulcer Disease

The present prophetic example is provided to outline a method by which the polyphosphorylated compounds (alcohols) of the present invention may be used to treat, as well as to prevent and inhibit, ulcer disease in humans.

The current recommended dose of sucralfate (sucroseoctasulfate and polyaluminum hydroxide) for humans is 1 g, 4×day (See Goodman and Gilmans Pharmacological Basis of Therapeutics, 18th edition, pg. 910). A dose of about 100 mg, 4×day of IHP and other polyphosphorylated alcohols is recommended. Therefore, since the present compositions are approximately 10-fold more potent than carafate in vivo (See Example 3), it is proposed that a dose of the phosphorylated alcohols of the present invention which would be effective for providing the gastro-protective action described herein would be an about 100 mg dose administered 4 times a day for a human.

While the phosphorylated and polyphosphorylated compounds of the present invention may be administered, at a neutral pH, through virtually any route sufficient to expose the stomach lining to the composition, those routes of administering most preferred for the treatment of a patient include oral routes (for example, in the form of a tablet or liquid preparation) as well as via enteral routes where the patient may not tolerate oral feeding or passage of substances.

BIBLIOGRAPHY

The following references insofar as they supplement the details of procedures detailed in the present disclosure, and provide for an even further enhanced understanding of the invention, are hereby specifically incorporated into the specification in pertinent part by reference.

1. E. Brady and G. Humiston, *General Chemistry*, John Wiley and Sons, N.Y., p. 179 (1982).
2. Tobey et al., (1986), *Am. J. Physiol.*, 255:G866–G869.
3. Davenport, (1966), *Gastroenterology*, 50:487-99.
4. WPI 82-00255403—Cent. Ind. Medicament (1980)
5. Stryer, (1986) In: *Biochemistry*, (3rd Ed.), pg. 338.
6. Ihre, B. J. E., (1970), *Acta Med. Scand. Supp.*, 95:1938.
7. Machen, et al., (1987), *Ann. Rev. Physiol.*, 49:19-33.
8. Sachs, et al., (1982), *J. Memb. Biol.*, 64:123-35.
9. Gutknecht, et al., (1981), *Biochim. Biophys. Acta*, 641:183-8.
10. Hope, et al., (1985), *Biochem. Phiophys. Acta.* 812:55–65.
11. Mayer, et al., (1986), *Biochim. Biophys. Acta*, 858:161-8.
12. Kano, et al., (1978), *Biochim. Biophys. Acta*, 509:289-99.
13. Biegel, et al., (1981), *Biochemistry*. 20:3473-9.
14. Dencher, et al., (1986), *Methods Enzymol.*, 127:754–6.
15. Krishnamoorthy, G., (1986), *Biochemistry*, 25:6666-71.
16. Deamer, D. W., (1987), *J. Bioenergetics and Biomembranes*, 19:457-79.
17. Shinitzky, et al., (1978), *Biochim. Biophys. Acta*, 515:367-94.
18. Dean, J. A. (ed), (1973), *Lange's Handbook of Chemistry*, 11th Edition, McGraw-Hill New York, p. 5-14.
19. Stryer, et al., (1988), 3rd ed., In: *Biochemistry*, p. 338-339.
20. J. Emsley and S. A. Niazi (1984) *Soil Biology and Biochemistry*, 16:73-76.
21. *Remington's Pharmaceutical Sciences*, 18th Ed. (190) Mack Publishing Company, Easton, Pa. 18042

What is claimed is:

1. A composition comprising a phosphorylated alcohol in combination with a polyvalent cation in a pharmacologically acceptable diluent.

2. The composition of claim 1, wherein the phosphorylated alcohol includes at least 3 phosphate groups.

3. The composition of claim 1, wherein the phosphorylated alcohol comprises glycerol triphosphate, threitol tetraphosphate, xylitol pentaphosphate or mannitol hexaphosphate.

4. The composition of claim 1, wherein the polyvalent cation is $Au^{+3}$, $Bi^{+3}$ or a mixture thereof.

5. The composition of claim 1, wherein the polyvalent cation is $Au^{+3}$.

6. The composition of claim 5, wherein the amount of $Au^{+3}$ is about 0.5 mM and the therapeutically effective amount of mannitol hexaphosphate is between about 100 mg/kg to about 50 mg/kg body weight.

7. The composition of claim 5 wherein the therapeutically effective amount of mannitol hexaphosphate is about 60 mg/kg body weight.

8. The composition of claim 4, wherein the polyvalent cation is $Bi^{+3}$ in an amount of about 1.0 mM.

9. The composition of claim 4, wherein the phosphorylated alcohol comprises mannitol hexaphosphate.

10. A method of protecting an animal in need thereof against ulcer disease comprising treating the animal with a composition comprising an anti-ulcer protective concentration of a phosphorylated alcohol in a pharmacologically acceptable diluent, wherein said method provides luminal protection against ulcerogenic agents.

11. The method of claim 10, wherein the phosphorylated organic molecule is a phosphorylated alcohol.

12. The method of claim 11, wherein the phosphorylated alcohol comprises a carbon chain of from 3 to 10 carbon atoms.

13. The method of claim 11, wherein the phosphorylated alcohol comprises a carbon chain of from 3 to 6 carbon atoms.

14. The method of claim 11, wherein the phosphorylated alcohol comprises inositol hexaphosphate, mannitol hexaphosphate, glycerol triphosphate, threitol tetraphosphate or xylitol pentaphosphate.

15. The method of claim 10, wherein the composition further comprises a polyvalent cation.

16. The method of claim 10, wherein the animal is a rat or a human.

17. The method of claim 10, wherein the phosphorylated organic alcohol comprises mannitol hexaphosphate, inositol hexaphosphate, glycerol triphosphate, threitol tetraphosphate, or xylitol pentaphosphate.

18. The method of claim 10, wherein the therapeutically effective concentration of the phosphorylated compound is between 60-1000 mg/kg body weight of the animal.

19. The method of claim 10, wherein the polyvalent cation is $Au^{+3}$ or $Bi^{+3}$.

20. A method of treating an animal with ulcer disease comprising treating the animal with a therapeutically effective amount of a composition comprising inositol hexaphosphate and a polyvalent cation.

21. The method of claim 20, wherein the cation is $Au^{+3}$, $Bi^{+3}$ or a combination thereof.

22. The method of claim 20, wherein the cation is $Au^{+3}$.

23. The method of claim 22, wherein the concentration of $Au^{+3}$ is about 0.5 mM.

24. The method of claim 22, wherein the polyvalent cation is $Bi^{+3}$.

25. The method of claim 24, wherein the concentration of $Bi^{+3}$ is about 1.0 mM.

26. The method of claim 20, wherein the therapeutically effective concentration of inositol hexaphosphate is between 50 and 1,000 mg/kg body weight of the animal.

27. The method of claim 20, wherein the therapeutically effective concentration of inositol hexaphosphate is about 60 mg/kg body weight of the animal.

28. The method of claim 20, wherein the animal is a rat or a human.

29. A method for preparing a formulation for the treatment of ulcer disease in an animal comprising combining an anti-ulcer protective concentration of a phosphorylated alcohol in combination with a polyvalent cation with a volume of distilled water sufficient to provide a therapeutically effective preparation for the treatment of ulcer disease.

30. The method of claim 29 wherein the therapeutically effective concentration of the phosphorylated alcohol is about 10 mg/ml.

31. A method for preparing a therapeutic agent for the treatment of ulcer disease comprising combining a precipitate of a phosphorylated alcohol with a quantity of a pharmacologically acceptable tableting material sufficient to provide an about 100 mg phosphorylated alcohol tablet concentration.

32. The method of claim 30 or 31 wherein the phosphorylated alcohol is inositol hexaphosphate, glycerol triphosphate, threitol tetraphosphate, xylitol pintophosphate or manitol hexaphosphate.

33. The method of claim 30 or 31 wherein the formulation or therapeutic agent comprises the polyvalent cation $Bi^{+3}$.

34. The method of claim 30 or 31 wherein the formulation or therapeutic agent comprises a polyvalent cation $Au^{+3}$ or $Bi^{+3}$.

35. A preparation for the treatment of ulcer disease consisting essentially of an anti-ulcer protective concentration of a per-phosphorylated alcohol and a polyvalent cation in a pharmaceutically acceptable diluent, wherein said preparation provides luminal protection against ulcerogenic agents.

36. The composition of claim 35 wherein the per-phosphorylated alcohol is inositol hexaphosphate.

37. A method of enhancing the resistance of a biological surface to ulcerogenic agents comprising treating an animal with a composition consisting essentially of an anti-ulcer protective concentration of a per-phosphylated alcohol in a pharmacologically acceptable diluent, wherein said composition provides luminal surface protection against ulcerogenic agents.

38. The method of claim 37 wherein the per-phosphorylated alcohol is inositol hexaphosphate.

39. The composition of claim 1 wherein the polyvalent cation is $Au^{+3}$, $Bi^{+3}$, $Ca^{+2}$, $Fe^{+2}$, $Fe^{+3}$, $Mg^{+2}$, $Al^{+2}$, or a mixture thereof.

40. The composition of claim 1 wherein the polyvalent cation is $Bi^{+3}$.

41. The preparation of claim 35 wherein the polyvalent cation is $Au^{+3}$, $Bi^{+3}$, $Ca^{+2}$, $Fe^{+2}$, $Fe^{+3}$, $Mg^{+2}$, $Al^{+3}$, or a mixture thereof.

42. The preparation of claim 35 wherein the polyvalent cation is $Au^{+3}$, $Bi^{+3}$, or a mixture thereof.

43. The preparation of claim 35 wherein the polyvalent cation is $Bi^{+3}$.

* * * * *

UNITED STATES PATENT AND TRADEMARK OFFICE
CERTIFICATE OF CORRECTION

PATENT NO. : 5,260,287
DATED : November 9, 1993
INVENTOR(S) : Barreto et al.

It is certified that error appears in the above-indentified patent and that said Letters Patent is hereby corrected as shown below:

In claim 9, line 20, column 19, delete "4," and substitute -- 1, -- therefor.

In claim 32, line 30, column 20, delete "pintophos-" and substitute -- pentaphos- -- therefor.

In claim 32, line 31, column 20, delete "manitol" and substitute -- mannitol -- therefor.

In claim 39, line 55, column 20, delete "Al$^{+2}$" and substitute -- Al$^{+3}$ -- therefor.

Signed and Sealed this

Twenty-first Day of June, 1994

Attest:

BRUCE LEHMAN

*Attesting Officer*  *Commissioner of Patents and Trademarks*